US011908550B2

(12) United States Patent
Liu et al.

(10) Patent No.: US 11,908,550 B2
(45) Date of Patent: Feb. 20, 2024

(54) METHOD FOR DETERMINING DIFFERENT PBDES DERIVATIVES FROM THEIR RESPONSE TO ACTIVITIES OF ENOYL-ACP REDUCTASE

(71) Applicant: Nanjing University, Nanjing (CN)

(72) Inventors: Hongling Liu, Nanjing (CN); Shuang Chen, Nanjing (CN); Laihao Shi, Nanjing (CN)

(73) Assignee: Nanjing University, Nanjing (CN)

( * ) Notice: Subject to any disclaimer, the term of this patent is extended or adjusted under 35 U.S.C. 154(b) by 540 days.

(21) Appl. No.: 17/093,580

(22) Filed: Nov. 9, 2020

(65) Prior Publication Data

US 2022/0119850 A1 Apr. 21, 2022

(30) Foreign Application Priority Data

Oct. 16, 2020 (CN) .......................... 202011111077.8

(51) Int. Cl.
*G16C 10/00* (2019.01)
*G16B 15/30* (2019.01)

(52) U.S. Cl.
CPC ............. *G16C 10/00* (2019.02); *G16B 15/30* (2019.02)

(58) Field of Classification Search
None
See application file for complete search history.

(56) References Cited

PUBLICATIONS

Carla Neckles et al. Rational Optimization of Diphenyl Ether Binding Kinetics to the Enoyl-ACP Reductase FabI1 from Burkholderia pseudomallei. Biochemistry. Apr. 4, 2017; 56(13): 1865-1878. (Year: 2017).*

Yang Wu et al. Qualitative and quantitative simulation of androgen receptor antagonists: A case study of polybrominated diphenyl ethers. Science of the Total Environment 603-604 (2017) 495-501 (Year: 2017).*

Hui Peng et al. An Unbiased Chemical Proteomics Method Identifies FabI as the Primary Target of 6-OH-BDE-47. Environ. Sci. Technol. 2016, 50, 11329-11336 (Year: 2016).*

Pharit Kamsri et al. Elucidating the structural basis of diphenyl ether derivatives as highly potent enoyl-ACP reductase inhibitors through molecular dynamics simulations and 3D-QSAR study. J Mol Model (2014) 20:2319 (Year: 2014).*

* cited by examiner

*Primary Examiner* — G. Steven Vanni
*Assistant Examiner* — Mary C Leverett
(74) *Attorney, Agent, or Firm* — Idea Intellectual Limited; Margaret A. Burke; Sam T. Yip

(57) ABSTRACT

The present invention provide a method of constructing a ligand-receptor protein complex to determine the binding activity of different PBDEs derivatives to an enoyl-ACP reductase. The method comprises providing a ligand-receptor binding complex, molecular docking and performing molecular dynamic simulation. The present invention is able to determine the binding activity of PBDEs derivatives to the enoyl-ACP reductase comparable to the results obtained in vitro.

4 Claims, 2 Drawing Sheets

METHOD FOR DETERMINING DIFFERENT PBDES DERIVATIVES FROM THEIR RESPONSE TO ACTIVITIES OF ENOYL-ACP REDUCTASE

CROSS-REFERENCES TO RELATED APPLICATIONS

This application claims priority from the Chinese Patent Application Number 202011111077.8 filed on Oct. 16, 2020, and the disclosure of which is incorporated herein by reference in its entirety.

FIELD OF THE INVENTION

The present invention relates to the technical field of organic pollutant identification, in particular, to a method for determining different PBDEs derivatives from their response to activities of enoyl-ACP reductase.

BACKGROUND OF THE INVENTION

It is necessary for organism to catalyze the fatty acid synthesis by fatty acid synthase. Fatty acid synthase is a complex enzyme system, which is able to catalyze the de novo synthesis of fatty acids from acetyl CoA and propionyl CoA in nature. In the fatty acid synthase system, fatty acid elongation is catalyzed by four enzymes, among which the enoyl-ACP reductase is the last step in fatty acid elongation, which is necessary to catalyze the reduction of enoyl-ACP to acyl carrier protein (ACP).

Polybrominated diphenyl ethers (PBDEs), as a kind of brominated flame retardant, have been widely used in various consumer products due to its excellent flame retardant properties. However, with the detection of PBDEs in environmental samples, the environmental problems initiated by PBDEs have attracted more and more attentions, especially in the field of environmental science. PBDEs have the characteristics of environmental persistence, long-distance transmission, bioaccumulation and toxic effects on organisms and human body. Researches to the environmental problems caused by PBDEs have become more popular in the field of environmental science.

The derivatives of polybrominated diphenyl ethers (PBDEs), including hydroxylated polybrominated diphenyl ethers (HO-PBDEs) and methoxylated polybrominated diphenyl ethers (MeO-PBDEs), have been widely detected in various environmental media.

At present, the binding activity of PBDEs derivatives to the enoyl-ACP reductase requires a series of tedious experiments to verify their activities. Therefore, there is a need to provide a fast, accurate and efficient method for determining the binding activities of different PBDEs derivatives to the enoyl-ACP reductase.

SUMMARY OF THE INVENTION

With respect to the above problems in the existing technology, the present invention provides a method for determining different PBDEs derivatives through constructing a ligand-receptor protein complex to determine the binding activity thereof to an enoyl-ACP reductase. The method includes:

providing a ligand and a modified enoyl-ACP reductase comprising: removing the B chain of the enoyl-ACP reductase and nicotinamide adenine dinucleotide (NAD+) bound to the B chain; removing all water molecules of the enoyl-ACP reductase to obtain the modified enoyl-ACP reductase with NAD+ only bound to the A chain thereof as a receptor; adding hydrogen atoms to NAD+ and Triclosan (TCS) of the modified enoyl-ACP reductase; constructing the structure of the ligand by a sketch module (Sketch Molecule module in sybyl7.3™); optimizing the structure of the ligand by a minimize module (Minimize module in sybyl7.3™);

docking the ligand to the receptor by performing a dock module (Surflex-Dock module in sybyl7.3™); generating at least one binding pocket of the receptor by using Ligand module; generating 20 conformations of the ligand when the ligand docks to the modified enoyl-ACP reductase; scoring the conformations to obtain the highest score conformation in terms of the docking quality, wherein the highest score conformation is identified as a potential biological conformation for molecular dynamic simulation;

performing at least one molecular dynamic simulation comprising: optimizing the structure of the ligand with a minimize module (Minimize module in sybyl7.3™) including using Powell method, giving Gasteiger-Hülckel charge as nuclear charge, storing said ligand in a database after said optimizing; undergoing 5000 steps of energy minimization before performing the molecular dynamic simulation; equilibrating energies of the ligand-receptor complex by NVT ensemble and NPT ensemble including simulating as 500 ps in the NVT ensemble, heating gradually from 0 to 300K under minimum energy, equilibrating under 500 ps at 300 K in the NPT ensemble, carrying out the molecular dynamic simulation and analysing hydrogen bond, π-π stacking and halogen bond interaction between the ligand and the receptor under 20 ns by Gromacs 5.1.2™, recording a trajectory thereof every 2ps.

In one embodiment of the present invention, said analysing the hydrogen bond, π-π stacking and halogen bond interaction between the ligand and the receptor includes determining whether the ligand forms hydrogen bond or π-π stacking to the NAD+ or a residue ALA196 of the modified enoyl-ACP reductase; if the ligand does not form hydrogen bond or π-π stacking to the NAD+ or the residue ALA196 of the modified enoyl-ACP reductase, analyzing the conformational change to determining whether a PRO154-ASN157 helix-loop region, a PHE251-ASN257 loop-helix region and a THR206-MET216 helix are adjacent to each other so as to close the binding pocket of the modified enoyl-ACP reductase.

In one embodiment of the present invention, said docking the ligand to the modified enoyl-ACP reductase comprises applying a threshold value of 0.5 and a bloat value of 0.

In one embodiment of the present invention, said generating at least one binding pocket of the modified enoyl-ACP reductase comprises providing the TCS as a positive substance so as to obtain the binding pocket of the modified enoyl-ACP reductase with centered binding sites generated by TCS; wherein the RMSD between the conformations generated by modified enoyl-ACP reductase bound to the Triclosan and conformations generated by a protein crystal structure of enoyl-ACP reductase bound to Triclosan is 0.72 Å.

In one embodiment of the present invention, said optimizing the structure with a minimize module (Minimize module in sybyl7.3™) using standard molecular force field (Tripos molecular force field of sybyl™) comprises applying a maximum number of iteration 100 times and a minimum energy change 0.05 KJ/mol.

In one embodiment of the present invention, said performing at least one molecular dynamic simulation further comprises:

applying Amber GAFF force field to the ligand and the NAD+ of the modified enoyl-ACP reductase including: applying Gaussian09 D01 to optimize the structure of the ligand and the NAD+ of the modified enoyl-ACP reductase;

calculating an electrostatic potential thereof, fitting restrained electrostatic potential (RESP) charge, generating RESP file via Antechamber module in Ambertools;

generating a Gromacs-compatible molecular topology file using a acpype.py script;

generating a protein topology file using pdb2gmx and using Amber99sb.ff as force field;

filling TIP3P water molecule in at least 2 nm away from the surface of the ligand-receptor protein complex to construct a box.

The beneficial effect of the invention: the results obtained by the method of the present invention are consistent with the experimental results of in vitro binding activity, suggesting that the method of the present invention is able to determine the binding activity of PBDEs derivatives to the enoyl-ACP reductase.

BRIEF DESCRIPTION OF THE DRAWINGS

The aspects of this disclosure will become more comprehensive from the following specific implementations with reference to the accompanying drawings. It should be noted that, various features may not be drawn to scale. Actually, the sizes of the various features may be increased or reduced arbitrarily for the purpose of clear description.

DETAILED DESCRIPTION

Figure 1:
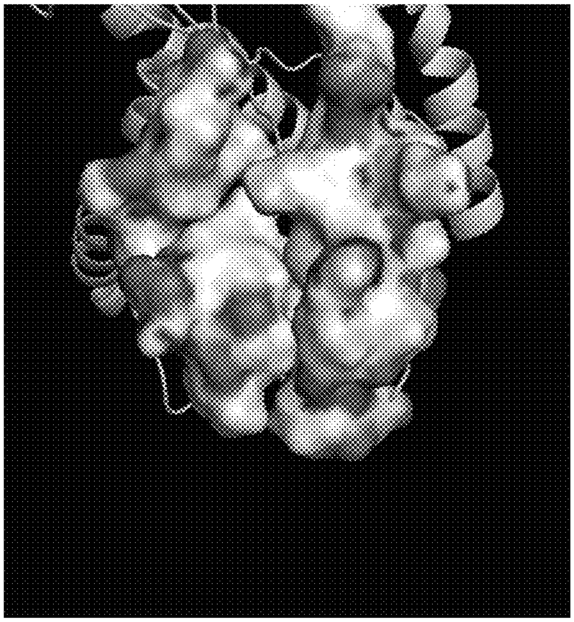
FIG. 1 shows the conformation under molecular dynamics simulation at 20 ns while TCS is provided as ligand.

In order to make the objectives, technical solutions, and advantages of the present invention clearer, the present invention will describe in more detail by the examples hereinafter to illustrate embodiments of the present. It should be understood that the specific embodiment described hereinafter are only used to explain the present invention, but not to limit the present invention.

In one aspect, there is provided a method to determine the inhibition activity of PBDEs derivatives against an enoyl-ACP reductase including:

(1) providing a ligand-receptor protein complex: a template for the protein structure of enoyl-ACP reductase (PDB ID: 1C14, FabI) is obtained from the RCSB protein data bank. Before docking between a ligand and a receptor, B chain of the enoyl-ACP reductase and nicotinamide adenine dinucleotide (NAD+) bound to the B chain are removed, followed by removing all water molecules from the enoyl-ACP reductase to obtain the modified enoyl-ACP reductase with NAD+only bound to the A chain thereof as a ligand. The modified enoyl-ACP reductase is used as a template for the molecular docking in the next step. Then, hydrogen atoms are added to NAD+ and Triclosan (TCS). All of the structures of the ligands (i.e. PBDEs derivatives and TCS as positive substance) are constructed by a sketch module (Sketch Molecule module in sybyl7.3™) and the structures of the ligands are optimized by a minimize module (Minimize module in sybyl7.3™);

(2) Molecules docking: the ligand is docked to the modified enoyl-ACP reductase by performing a dock module (Surflex-Dock module in sybyl7.3™). While docking, the Ligand mode is used; and the TCS is used as a positive substance to obtain the binding pocket of the modified enoyl-ACP reductase with the centered binding sites generated by the TCS. During the docking between the ligands and the modified enoyl-ACP reductase, the threshold value is 0.5, and the bloat value is 0.

Comparing the structures after molecular docking with the protein crystal structures bond to TCS, the difference between these two structures was small. The RMSD (root mean square deviation) between the predicted conformation and the real conformation is only 0.72 Å, which is less than the X-ray crystallographic resolution (2.2 Å), suggesting the reliability of the parameter setting and docking results in the docking process.

Considering the flexibility of the ring, each ligand compound would generate 20 binding conformations. The conformation with the highest score is regarded as the most likely bioactive conformation for further molecular dynamics simulation. The structural and functional relationships are affected by the conformation after binding, which is related to the interaction between ligand and receptor. Referring to Table 1, it showed the interaction of hydrogen bond, π-π stacking and halogen bond between ligand and receptor after molecular docking comparing to the in vitro measurement of the binding activity of the ligands (PBDEs derivatives) and receptors (enoyl-ACP reductase).

TABLE 1

The interaction of hydrogen bond, π-π stacking and halogen bond between ligand and receptor and *in vitro* measurement of the binding activity

| Name | H-bond | π-π stack | Halogen bond | *in vitro* measurement of the binding activity |
|---|---|---|---|---|
| 2OHBDE123 | GLY93 | PHE94 | NO | No inhibition |
| 4MeOBDE17 | NO | PHE94, ALA196 | NO | No inhibition |
| 4OHBDE49 | NO | NO | NO | inhibition |
| 5MeOBDE47 | NO | PHE94 | NO | No inhibition |
| 6MeOBDE17 | NO | PHE94 | NO | No inhibition |
| 6MeOBDE47 | NO | PHE94 | NO | No inhibition |
| 6MeOBDE85 | NO | PHE94 | NO | No inhibition |
| 6MeOBDE90 | NO | NO | NO | No inhibition |
| 6OHBDE17 | NAD+ | NO | NO | Inhibit |
| 6OHBDE47 | NAD+ | NAD+, TYR146 | NO | Inhibit |
| 6OHBDE90 | PHE94 | PHE94 | NO | Inhibit |
| 6OHBDE137 | PHE94 | PHE90 | NO | Inhibit |
| 6OHClBDE17 | NO | NO | NO | Inhibit |
| 6OHClBDE68 | NO | PHE94 | NO | Inhibit |
| TCS | ALA95, TYR 156, NAD+ | TYR146, ALA1 96 | NO | Inhibit |

According to Table 1, the conformations docked with each ligand (PBDEs derivatives) are similar to the conformation docked with TCS. However, their interactions with protein receptor are different. Most ligands interact with the residue PHE94 of the receptor, but the molecular docking fails to determine or differentiate the inhibition ability of the ligands to the receptors.

(3) Molecular dynamic (MD) simulation includes: (a) under the force field (Tripos force field of Sybyl™), the ligands in Table 1 were optimized through the molecular mechanics program minimize by using Powell method, and giving Gasteiger-Hückel charge. The maximum number of interation is 100 and the minimum energy change is 0.05 KJ/mol. Then the optimized ligands were saved in the database and the binding sites generated by the TCS were used as the binding pocket of the receptor; (b) MD simulation by Gromacs 5.1.2: performing 5000 steps of energy minimization before performing the molecular dynamic simulation; equilibrating energies of the ligand-protein complex by NVT ensemble and NPT ensemble including simulating as 500 ps in the NVT ensemble; heating gradually from 0 to 300 K under minimum energy; equilibrating energies under 500 ps at 300 K in the NPT ensemble; carrying out the molecular dynamic simulation under 20 ns and recording the trajectory every 2 ps.

In order to evaluate the stability of the ligand-receptor complex in MD simulation, the root mean square deviation (RMSD) of the complex coordinates was calculated. The change of RMSD showed that all complex reach equilibrium before 20 ns. The RMSD value of each complex was less than 0.25 nm. By analyzing the fluctuation of each of amino acid residues of the receptor protein in 20 ns, it was found that the fluctuation of the residues mainly in ASP98-ALA197 loop region, PRO154-ASN157 loop region and THR194-MET206 helix-loop in binding pocket during MD simulation, indicating these amino acid residues change greatly and are flexible in MD simulation.

During the simulation process, Amber GAFF force field was applied to the ligands and cofactor NAD+molecules in the receptor molecules. Gaussian09 DO1 was used to optimize the structure of the ligand and the NAD+ of the receptor followed by calculating an electrostatic potential, fitting RESP charge, and generating RESP file via Antechamber module in Ambertools. Then, a Gromacs-compatible molecular topology file was generated by using acpype.py script followed by generating a protein topology file using pdb2gmx and using Amber99sb.ff as a force field. The box is constructed at least 2 nm away from the surface of the ligand-protein complex, and then TIP3P water molecules is filled in, i.e. there is at least 2 nm at the margin of protein complex. As shown in table 2, the hydrogen bond, π-π stacking and halogen bond interaction between ligand and receptor were analyzed at 20 ns simulation, and the results were compared to the in vitro measured binding activity of receptor (enoyl-ACP reductase) to the PBDEs derivatives.

TABLE 2

The hydrogen bond, π-π stacking, halogen bond and hydrophic interation between ligand and receptor and in vitro measurement of the binding activity

| Names | H-bond | π-π stack | Halogen bond | Hydrophobic | *in vitro* measurement of the binding activity |
|---|---|---|---|---|---|
| 2OHBDE123 | GLY93 | NO | NO | ALA15,TYR156,MET159,LEU195,ALA196,ILE200 | No inhibit |
| 4MeOBDE17 | NO | NO | NO | TYR156,MET159,ALA196,ALA197,ILE200,PHE203 | No inhibit |
| 4OHBDE49 | NO | NO | NO | LEU100,TYR146,ILE153,MET159,LYS163,ALA196,ALA197,PHE203 | inhibit |
| 5MeOBDE47 | NO | NO | PHE94 | ALA15,LEU100,LEU195,ALA196,ILE200 | No inhibit |
| 6MeOBDE17 | NO | NO | NO | ARG193,ALA197,ARG204,LEU207 | No inhibit |
| 6MeOBDE47 | NO | NO | ALA95 | PHE94,ALA196,ALA197,ILE200,PHE203,NAD+ | No inhibit |
| 6MeOBDE85 | NO | NO | GLY199 | LEU100,MET159,LEU195,ALA196,ILE200,NAD+ | No inhibit |
| 6MeOBDE90 | NO | NO | ALA95 | PHE94,LEU100,MET159,ALA196,ILE200,NAD+ | No inhibit |
| 6OHBDE17 | NAD+ | NAD+ | NO | LEU100,TYR156,MET159,ALA197,ILE200 | Inhibit |
| 6OHBDE47 | NAD+,TYR156 | TYR146 | NO | MET159,PRO191,ALA196,ALA197,ILE200,PHE203 | Inhibit |
| 6OHBDE90 | ALA196 | NO | NO | ALA15,LEU100,MET159,ALA197,ILE200 | Inhibit |
| 6OHBDE137 | ALA196 | NO | NAD+, ASN155 | ILE92,LEU100,TYR156,MET159,ILE200 | Inhibit |
| 6OHClBDE17 | NAD+ | TYR146, ALA196 | NO | LEU100,TYR146,TYR156,MET159,ALA197,ILE200 | Inhibit |
| 6OHClBDE68 | NAD+ | NAD+ | NO | LEU195,ALA196 | Inhibit |
| TCS | ALA95, TYR156, NAD+ | TYR146, ALA196 | NO | MET159,PRO191,ALA197,ILE200,PHE203,MET206 | Inhibit |

As shown in table 2, most of the ligands with inhibition activity to the receptor (enoyl-ACP reductase) will form hydrogen bonds or π-π stacking with NAD+ or ALA196, which is the key factor to predict the binding of ligand to receptor. However, there is one exception: the ligand 4OHBDE49 is able to inhibit the receptor enoyl-ACP reductase, but it has no obvious interaction with NAD+ or ALA196.

Figure 2:
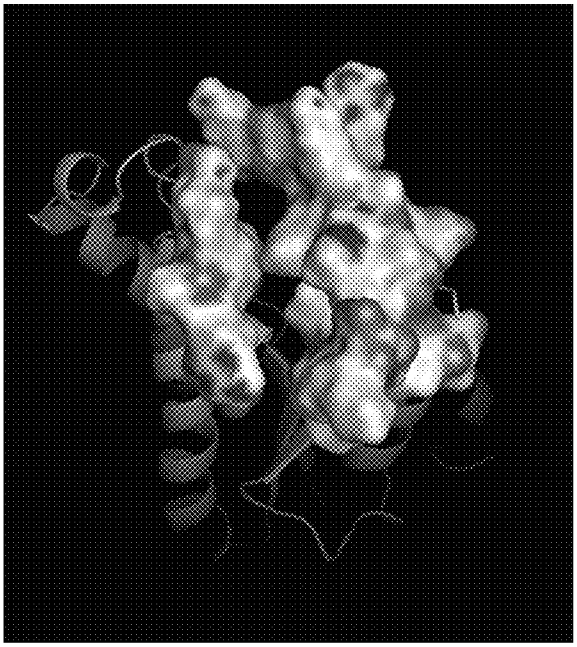
FIG. 2 shows the conformation under molecular dynamics simulation at 0 ns while TCS is provided as ligand.
Figure 3:
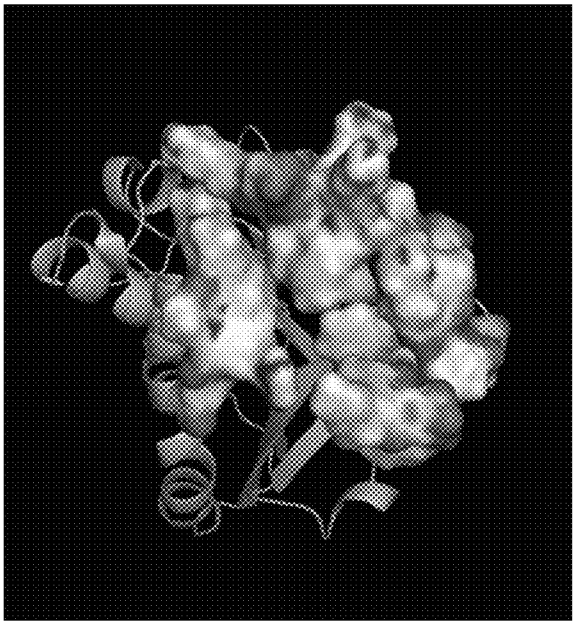
FIG. 3 shows the conformation under molecular dynamics simulation at 20 ns while 6MeOBDE17 is provided as ligand.

(c) Analysis of the conformation changes: after binding the receptor to the ligand with inhibition ability, the helix-loop region of ASP98-ALA197, the helix-loop region of PRO154-ASN157 and the helix-loop region of THR194-MET206 in the binding pocket changed from helical structure to regular curl structure or the helix was shorten. Further, PRO154-ASN157 helix-loop region, PHE251-ASN257 loop-helix region and THR206-MET216 helix region are adjacent to each other. Since the amino acid segment is the channel for substrate to enter the active site, the proximity of these regions makes the entrance of the binding pocket of the receptor closer so as to block the acyl group from entering the active site, thus resulting in inhibition. As shown in FIGS. 1 to 3, most ligands with no binding ability have no such conformational changes. Referring to FIG. 1, TCS was used as ligand. The above mentioned regions were close to each other and the pocket entrance was closed at 20 ns during the molecular dynamics simulation, such that TCS was expected to inhibit the receptor. Referring to FIG. 2, the conformation of the pocket entrance was open at 0 ns (initial status) during the molecular dynamics. Referring to FIG. 3, 6MeOBDE17 was used as ligand. The pocket entrance was open at 20 ns during the molecular dynamics simulation, suggesting that 6MeOBDE17 has no inhibition ability. Due to the proximity of PRO154-ASN157 helix-loop region, PHE251-ASN257 loop-helix region and THR206-MET216 helix region of the receptor caused by the ligand 4OHBDE49, the pocket entrance is closed and acyl group is blocked from entering the active site. Although 4OHBDE49 did not form hydrogen bonds or π-π stacking with NAD+ or ALA196, it is still able to inhibit the receptor.

The in vitro binding activity assay was as follows: overexpression of His-labeled FabI in the *E. coli* lysate was prepared. When the bacterial optical density (OD600) reached 0.6, the expression was induced overnight with 1 mm IPTG at 16° C. Then, the bacteria were collected and washed once with PBS. The bacteria were lysed in the lysis buffer containing 500 mM NaCl, 10 mm Tris HCl and 0.1% NP-40 (pH=8.5). FabI was purified from the supernatant with Ni-NTA agarose (Qiagen) and centrifuged at 14000 g for 30 min. The resin containing Ni-NTA was transferred to a Poly-Prep column (Bio-Red) and equilibrated twice with washing buffer (50 mm PBS, pH 8.2, 300 mM NaCl and 10 mm imidazole). After incubation with FabI lysate at 4° C. for 30 minutes, the resin was washed twice with a washing buffer, and the FabI protein was eluted with a buffer containing 50 mm PBS, pH 8.2, 300 mM NaCl and 250 mm imidazole. 300 μM butyl coenzyme A was added and followed by adding the mixture of 100 nM recombinant FabI, 400 μM NADH and 40 μM NAD+. The oxidation rate of NADH to NAD+ was measured every 2 minutes with a microplate reader at 340 nm. In order to determine the inhibition ability of PBDEs derivatives to the FabI enzyme activity, PBDEs with different concentrations (0.014-10 μM) were incubated with 100 nM recombinant FabI on ice for 60 minutes, and then the oxidation rate of NADH to NAD+ was determined.

In conclusion, the present invention provides a method of constructing a ligand-receptor protein complex to determine the binding activity of PBDEs derivatives to an enoyl-ACP reductase. The method comprises providing a ligand-receptor binding complex, molecular docking and performing molecular dynamic simulation. The molecular dynamics simulation includes ligand optimization, analysis of hydrogen bond and π-π stacking interaction between the ligand and receptor at 20 ns so as to determine whether the ligand forms hydrogen bond or π-π stacking with NAD+ or ALA196. If the above interaction is formed, it will suggest that the ligands are able to inhibit the receptor. If the above interaction is not formed, then the conformational changes will be further analyzed to determine whether the receptor's binding pocket entrance is closed due to the proximity of PRO154-ASN157 helix-loop region, PHE251-ASN257 helix-loop region and THR206-MET216 helix. The ligands are able to have inhibition ability in the presence of the above regions/helix. The ligands of PBDEs derivatives of the present invention include 2OHBDE123, 4MeOBDE17, 4OHBDE49, 5MeOBDE47, 6MeOBDE17, 6MeOBDE47, 6MeOBDE85, 6MeOBDE90, 6OHBDE17, 6OHBDE47, 6OHBDE90, 6OHBDE137, 6OHClBDE17, and 6OHClBDE68. The results obtained by the method of the present invention are consistent with the experimental results of in vitro binding activity, suggesting that the method of the present invention is able to determine the binding activity of PBDEs derivatives to the enoyl-ACP reductase.

The above descriptions are only preferred embodiments of the present invention and are not intended to limit the present invention. Any modification, equivalent replacement and improvement made within the spirit and principle of the present invention shall be included in the protection of the present invention.

What is claimed is:

1. A method of constructing a ligand-receptor protein complex for determining different polybrominated diphenyl ethers derivatives in terms of binding activity thereof to enoyl-ACP reductase, said method comprising:

providing a ligand and a modified enoyl-ACP reductase comprising: removing the B chain of the enoyl-ACP reductase and nicotinamide adenine dinucleotide bound to the B chain; removing all water molecules attached to the enoyl-ACP reductase to obtain the modified enoyl-ACP reductase with nicotinamide adenine dinucleotide only bound to the A chain thereof; adding hydrogen atoms to the nicotinamide adenine dinucleotide of the A chain and a positive substance, wherein the positive substance is Triclosan; computationally constructing a structure of the ligand; computationally optimizing the structure of the ligand;

computationally docking the ligand to the modified enoyl-ACP reductase; computationally generating at least one binding pocket of the modified enoyl-ACP reductase; generating 20 conformations of the ligand-receptor complex after the ligand docks to the modified enoyl-ACP reductase; scoring the conformations to obtain the highest score conformation, wherein the highest score conformation is identified as a potential bioactive conformation for one or more subsequent molecular dynamic simulations;

performing at least one molecular dynamic simulation comprising: computationally optimizing the structure of the ligand including using Powell method to optimize, giving Gasteiger-Hückel charge as nuclear charges, using a molecular force field, saving optimized ligand structure in a database; undergoing 5000 steps of energy minimization before performing the molecular dynamic simulation; equilibrating energies of the complex by NVT ensemble and NPT ensemble including simulating as 500 ps in the NVT ensemble; heating gradually from 0 to 300 K under a minimum energy; further equilibrating the energies under 500 ps at 300 K in the NPT ensemble; carrying out the molecular dynamic simulation and analysing hydrogen bond, π-π stacking and halogen bond interaction under 20 ns; recording a trajectory of the simulation every 2 ps;

wherein said analysing the hydrogen bond, π-π stacking and halogen bond interaction includes determining whether the ligand forms hydrogen bond or π-π stacking to the nicotinamide adenine dinucleotide or a residue ALA196 of the modified enoyl-ACP reductase, and wherein if the ligand does not form hydrogen bond or π-π stacking to the nicotinamide adenine dinucleotide or the residue ALA196 of the modified enoyl-ACP reductase, analyzing the conformational change to determining whether a PRO154-ASN157 helix-loop region, a PHE251-ASN257 loop-helix region and a THR206-MET216 helix are adjacent to each other so as to close the binding pocket of the modified enoyl-ACP reductase;

wherein the generating at least one binding pocket of the modified enoyl-ACP reductase further comprises providing Triclosan as a positive substance so as to obtain a simulated binding pocket of the modified enoyl-ACP reductase bound to the Triclosan, wherein the modified enoyl-ACP reductase forms a receptor binding pocket around the binding site to the Triclosan; wherein a root mean square deviation is determined between the conformations of the simulated binding pocket of the modified enoyl-ACP reductase bound to the Triclosan and actual conformations of the binding pocket of an enoyl-ACP reductase;

wherein the performing at least one molecular dynamic simulation further comprises applying a generalized force field to the ligand and the nicotinamide adenine dinucleotide of the modified enoyl-ACP reductase including: optimizing the structure of the ligand and the nicotinamide adenine dinucleotide of the modified enoyl-ACP reductase;

computationally calculating an electrostatic potential thereof, fitting restrained electrostatic potential charge, generating restrained electrostatic potential file;

generating a molecular topology file;

generating a protein topology file as a force field; and filling TIP3P water molecule in at least 2 nm away from the surface of the ligand-receptor protein complex to construct a box.

2. The method of claim 1, wherein said optimizing the structure with the minimize module using the molecular force field comprises applying a maximum number of iteration of 100 times and a minimum energy change at 0.05 KJ/mol.

3. The method of claim 1, wherein the ligand includes one or more polybrominated diphenyl ethers derivatives selected from 2OHBDE123, 4MeOBDE17, 4OHBDE49, 5MeOBDE47, 6MeOBDE17, 6MeOBDE47, 6MeOBDE85, 6MeOBDE90, 6OHBDE17, 6OHBDE47, 6OHBDE90, 6OHBDE137, 6OHClBDE17, and 6OHClBDE68.

4. The method of claim 1, wherein the enoyl-ACP reductase is FabI.

* * * * *